US012350156B2

(12) United States Patent
Raanani et al.

(10) Patent No.: US 12,350,156 B2
(45) Date of Patent: Jul. 8, 2025

(54) ATRIOVENTRICULAR VALVE REPAIR

(71) Applicant: Sheba Impact Ltd., Ramat Gan (IL)

(72) Inventors: Ehud Raanani, Hod Hasharon (IL);
Boris Orlov, Rishon Letzion, IL (US)

(73) Assignee: Sheba Impact Ltd., Ramat Gan (IL)

( * ) Notice: Subject to any disclaimer, the term of this patent is extended or adjusted under 35 U.S.C. 154(b) by 832 days.

(21) Appl. No.: 17/292,987

(22) PCT Filed: Nov. 13, 2019

(86) PCT No.: PCT/IB2019/059734
§ 371 (c)(1),
(2) Date: May 11, 2021

(87) PCT Pub. No.: WO2020/100050
PCT Pub. Date: May 22, 2020

(65) Prior Publication Data
US 2022/0015905 A1   Jan. 20, 2022

Related U.S. Application Data

(60) Provisional application No. 62/767,018, filed on Nov. 14, 2018.

(51) Int. Cl.
*A61F 2/24* (2006.01)
*A61B 17/02* (2006.01)

(52) U.S. Cl.
CPC .......... *A61F 2/2466* (2013.01); *A61F 2/2445* (2013.01); *A61B 17/0218* (2013.01)

(58) Field of Classification Search
CPC .... A61F 2/2466; A61F 2/2445; A61F 2/2412; A61F 2220/0008; A61F 2250/006; A61F 2/2457; A61B 17/0218
See application file for complete search history.

(56) References Cited

U.S. PATENT DOCUMENTS

| 6,270,520 B1 | 8/2001 | Inoue |
| 7,018,408 B2 | 3/2006 | Bailey et al. |
(Continued)

FOREIGN PATENT DOCUMENTS

| CA | 2606101 A1 | 11/2006 |
| CA | 2898991 A1 | 8/2014 |
(Continued)

OTHER PUBLICATIONS

Extended European Search Report for European Application No. 23162937.9 mailed Jun. 21, 2023.
(Continued)

*Primary Examiner* — Jerrah Edwards
*Assistant Examiner* — Jose H. Trevino, III
(74) *Attorney, Agent, or Firm* — Dorsey & Whitney LLP (57) ABSTRACT

Apparatus and methods are described for use with an annuloplasty ring (20), and an atrioventricular valve of a heart of a mammalian subject, the atrioventricular valve including a valve annulus, valve leaflets, chords, and papillary muscles. A plurality of chord-manipulation arms (26) are configured to be deployed among the chords of the atrioventricular valve, and to cause a size of the valve annulus to decrease, by the chord-manipulation arms (26) being rotated such as to twist the native atrioventricular valve and pull the native atrioventricular valve radially inwards, by the chord-manipulation arms (26) deflecting the chords. The chord-manipulation arms (26) are configured to subsequently provide a counterforce against which the annuloplasty ring (20) is pushed, during implantation of the annuloplasty ring (20). Other applications are also described.

19 Claims, 9 Drawing Sheets

(56) References Cited

U.S. PATENT DOCUMENTS

| | | | |
|---|---|---|---|
| 7,621,948 B2 | 11/2009 | Herrmann et al. | |
| 7,748,389 B2 | 7/2010 | Salahieh et al. | |
| 7,753,949 B2 | 7/2010 | Lamphere et al. | |
| 8,070,802 B2 | 12/2011 | Lamphere et al. | |
| 8,870,950 B2 | 10/2014 | Hacohen | |
| 9,364,326 B2 | 6/2016 | Yaron | |
| 9,700,412 B2 | 7/2017 | Yaron et al. | |
| 9,949,830 B2 | 4/2018 | Solem | |
| 10,105,217 B2 | 10/2018 | Keränen | |
| 10,130,471 B2 | 11/2018 | Keränen et al. | |
| 10,238,489 B2 | 3/2019 | Conklin | |
| 10,292,816 B2 | 5/2019 | Raanani et al. | |
| 10,292,850 B2 | 5/2019 | Vad et al. | |
| 10,500,038 B1 | 12/2019 | Orlov et al. | |
| 11,065,114 B2 | 7/2021 | Raanani et al. | |
| 11,583,394 B2 | 2/2023 | Orlov et al. | |
| 11,779,459 B2 | 10/2023 | Raanani et al. | |
| 2002/0065554 A1 | 5/2002 | Streeter | |
| 2003/0014104 A1 | 1/2003 | Cribier | |
| 2003/0083742 A1 | 5/2003 | Spence et al. | |
| 2004/0138745 A1 | 7/2004 | Macoviak et al. | |
| 2005/0165479 A1 | 7/2005 | Drews et al. | |
| 2006/0195134 A1 | 8/2006 | Crittenden | |
| 2006/0195184 A1 | 8/2006 | Lane et al. | |
| 2006/0241745 A1 | 10/2006 | Solem | |
| 2007/0016288 A1 | 1/2007 | Gurskis et al. | |
| 2007/0050020 A1 | 3/2007 | Spence | |
| 2007/0260305 A1 | 11/2007 | Drews et al. | |
| 2008/0039935 A1 | 2/2008 | Buch et al. | |
| 2009/0192585 A1 | 7/2009 | Bloom et al. | |
| 2009/0192586 A1 | 7/2009 | Tabor et al. | |
| 2009/0198324 A1 | 8/2009 | Orlov | |
| 2010/0022640 A1 | 1/2010 | Stoutamire | |
| 2010/0042208 A1 | 2/2010 | Herrmann et al. | |
| 2010/0049313 A1 | 2/2010 | Alon et al. | |
| 2010/0249923 A1 | 9/2010 | Alkhatib et al. | |
| 2010/0331971 A1 | 12/2010 | Keraenen et al. | |
| 2011/0029072 A1 | 2/2011 | Gabbay | |
| 2011/0137397 A1 | 6/2011 | Chau et al. | |
| 2011/0137410 A1 | 6/2011 | Hacohen | |
| 2011/0224785 A1 | 9/2011 | Hacohen | |
| 2011/0264208 A1 | 10/2011 | Duffy et al. | |
| 2012/0010461 A1 | 1/2012 | Goldfarb et al. | |
| 2012/0022639 A1 | 1/2012 | Hacohen et al. | |
| 2012/0022640 A1 | 1/2012 | Gross et al. | |
| 2012/0101571 A1 | 4/2012 | Thambar et al. | |
| 2013/0035759 A1 | 2/2013 | Gross et al. | |
| 2013/0166022 A1 | 6/2013 | Conklin | |
| 2014/0031928 A1 | 1/2014 | Murphy et al. | |
| 2014/0088695 A1 | 3/2014 | Figulla et al. | |
| 2014/0088696 A1 | 3/2014 | Figulla et al. | |
| 2014/0222136 A1 | 8/2014 | Geist et al. | |
| 2014/0379074 A1* | 12/2014 | Spence | A61F 2/2418 623/2.11 |
| 2015/0045880 A1 | 2/2015 | Hacohen | |
| 2015/0173897 A1* | 6/2015 | Raanani | A61F 2/2436 623/2.11 |
| 2015/0351903 A1 | 12/2015 | Morriss et al. | |
| 2015/0351908 A1 | 12/2015 | Kernen et al. | |
| 2015/0359628 A1 | 12/2015 | Keränen | |
| 2015/0374493 A1 | 12/2015 | Yaron et al. | |
| 2016/0045306 A1 | 2/2016 | Agrawal et al. | |
| 2016/0095705 A1 | 4/2016 | Keränen et al. | |
| 2017/0128199 A1 | 5/2017 | Gurovich et al. | |
| 2017/0281338 A1 | 10/2017 | Quill et al. | |
| 2018/0014932 A1 | 1/2018 | Hammer et al. | |
| 2018/0125651 A1 | 5/2018 | Nasr | |
| 2018/0177594 A1 | 6/2018 | Patel et al. | |
| 2018/0206992 A1 | 7/2018 | Brown | |
| 2019/0083245 A1 | 3/2019 | Hariton et al. | |
| 2019/0110893 A1 | 4/2019 | Haarer et al. | |
| 2019/0125534 A1 | 5/2019 | Arcaro et al. | |
| 2019/0231520 A1 | 8/2019 | Desrosiers et al. | |
| 2019/0231522 A1 | 8/2019 | Raanani et al. | |
| 2020/0100898 A1 | 4/2020 | Vola et al. | |
| 2020/0121454 A1 | 4/2020 | Spence | |
| 2020/0197175 A1 | 6/2020 | Chang et al. | |
| 2022/0010634 A1 | 1/2022 | Posa | |
| 2022/0015896 A1 | 1/2022 | Agian et al. | |
| 2022/0015905 A1 | 1/2022 | Raanani et al. | |
| 2022/0296370 A1 | 9/2022 | Agian et al. | |
| 2023/0000622 A1 | 1/2023 | Raanani et al. | |
| 2023/0172707 A1 | 6/2023 | Orlov et al. | |

FOREIGN PATENT DOCUMENTS

| | | |
|---|---|---|
| CN | 101180010 A | 5/2008 |
| CN | 102292053 A | 12/2011 |
| CN | 102438546 A | 5/2012 |
| CN | 104684505 A | 6/2015 |
| CN | 104994812 A | 10/2015 |
| DE | 102006052564 | 12/2007 |
| EP | 1850796 B1 | 12/2015 |
| EP | 3399947 A1 | 11/2018 |
| EP | 2948102 B1 | 1/2019 |
| EP | 2852354 B1 | 5/2020 |
| JP | 2008536592 A | 9/2008 |
| JP | 2011509806 A | 3/2011 |
| JP | 2012500665 A | 1/2012 |
| JP | 2012521222 A | 9/2012 |
| JP | 2014168694 A | 9/2014 |
| JP | 2015517376 A | 6/2015 |
| JP | 2016504134 A | 2/2016 |
| JP | 2018501001 A | 1/2018 |
| JP | 2019500965 A | 1/2019 |
| JP | 7051736 B2 | 4/2022 |
| WO | 0060995 A2 | 10/2000 |
| WO | 2004032724 A2 | 4/2004 |
| WO | 2005087140 A1 | 9/2005 |
| WO | 2006116558 A2 | 11/2006 |
| WO | 2007135101 A1 | 11/2007 |
| WO | 2009134701 A2 | 11/2009 |
| WO | 2010108079 A1 | 9/2010 |
| WO | 2012004679 A2 | 1/2012 |
| WO | 2012095116 A1 | 7/2012 |
| WO | 2013001339 A2 | 1/2013 |
| WO | 2013175468 A2 | 11/2013 |
| WO | 2014114795 A1 | 7/2014 |
| WO | 2015198125 A1 | 12/2015 |
| WO | 2018109329 A1 | 6/2018 |
| WO | 2018112429 A1 | 6/2018 |
| WO | 2020092096 A2 | 5/2020 |
| WO | 2020100050 A1 | 5/2020 |
| WO | 2021028867 A1 | 2/2021 |
| WO | 2022090881 A1 | 5/2022 |
| WO | 2022090882 A1 | 5/2022 |
| WO | 2022234468 A1 | 11/2022 |
| WO | 2022264082 A1 | 12/2022 |
| WO | 2023228028 A1 | 11/2023 |
| WO | 2024057226 A1 | 3/2024 |

OTHER PUBLICATIONS

Notice of Allowance for U.S. Appl. No. 17/349,152 mailed May 24, 2023.
Office Action for Canadian Application No. 3,149,527 mailed Mar. 6, 2023.
U.S. Appl. No. 16/106,000, filed Oct. 27, 2020.
U.S. Appl. No. 16/106,034, filed Oct. 27, 2020.
U.S. Appl. No. 18/248,394, filed Apr. 10, 2023.
U.S. Appl. No. 63/106,000, filed Oct. 27, 2020.
U.S. Appl. No. 63/106,034, filed Oct. 27, 2020.
Advisory Action for U.S. Appl. No. 14/402,387 mailed Mar. 1, 2018.
Communication Pursuant to Article 94(3) EPC Dated Jan. 8, 2018 From the European Patent Office Re. Application No. 13732633.6.
Communication Relating to the Results of the Partial International Search Dated Nov. 18, 2013 From the International Searching Authority Re. Application No. PCT/IL2013/050432.
Corrected Notice of Allowability for U.S. Appl. No. 14/402,387 mailed Mar. 20, 2019.

(56) References Cited

OTHER PUBLICATIONS

Examination Report for Australian Application No. 2013264730 mailed Dec. 20, 2017.
Examination Report for Australian Application No. 2013264730 mailed Jan. 13, 2017.
Examination Report for Australian Application No. 2018202951 mailed Dec. 6, 2018.
Examination Report for Australian Application No. 2019250140 mailed Oct. 19, 2020.
Examination Report for European Application No. 13732633.6 mailed Aug. 8, 2019.
Examination Report for Indian Application No. 2424/MUMNP/2014 mailed Aug. 31, 2020.
Final Office Action for U.S. Appl. No. 14/402,387 mailed Oct. 2, 2017.
Final Office Action for U.S. Appl. No. 13/475,994 mailed Jan. 10, 2017.
Final Office Action for U.S. Appl. No. 13/475,994 mailed Jun. 10, 2015.
International Preliminary Report on Patentability from International Application No. PCT/IL2013/050432 mailed Dec. 4, 2014.
International Search Report and Written Opinion from International Application No. PCT/IB2019/059734 mailed Feb. 6, 2020.
International Search Report and Written Opinion from International Application No. PCT/IB2020/057636 mailed Oct. 29, 2020.
International Search Report and Written Opinion from International Application No. PCT/IL2013/050432 mailed Feb. 26, 2014.
Issue Notification for U.S. Appl. No. 14/402,387 mailed May 1, 2019.
Non-Final Office Action for U.S. Appl. No. 13/475,994 mailed Apr. 1, 2016.
Non-Final Office Action for U.S. Appl. No. 13/475,994 mailed Oct. 1, 2014.
Non-Final Office Action for U.S. Appl. No. 13/475,994 mailed Sep. 11, 2017.
Non-Final Office Action for U.S. Appl. No. 14/402,387 mailed Dec. 23, 2016.
Non-Final Office Action for U.S. Appl. No. 14/402,387 mailed Sep. 20, 2018.
Notice of Allowance for U.S. Appl. No. 14/402,387 mailed Apr. 30, 2019.
Notice of Allowance for U.S. Appl. No. 14/402,387 mailed Jan. 30, 2019.
Notice of Allowance for U.S. Appl. No. 16/374,240 mailed Mar. 16, 2021.
Notice of Amendment Dated Jun. 23, 2017 From the State Intellectual Property Office of the People's Republic of China Re. Application No. 201710425696.6 and Its Machine Translation Into English.
Notice of Reason for Rejection Dated Feb. 14, 2017 From the Japan Patent Office Re. Application No. 2015-513347 and Translation.
Notification of Office Action and Search Report Dated Sep. 7, 2016 From the State Intellectual Property Office of the People's Republic of China Re. Application No. 201380038199.0.
Notification of Office Action Dated Dec. 3, 2015 From the State Intellectual Property Office of the People's Republic of China Re. Application No. 201380038199.0.
Notification of Office Action Dated Dec. 14, 2016 From the State Intellectual Property Office of the People's Republic of China Re. Application No. 201380038199.0 and Its Translation Into English.
Office Action for Australian Application No. 2018202951 mailed Apr. 1, 2019.
Office Action for Canadian Application No. 2,874,208 mailed Aug. 2, 2019.
Office Action for Canadian Application No. 2,874,208 mailed Feb. 19, 2019.
Office Action for Chinese Application No. 201710425696.6 mailed May 19, 2020.
Office Action for Chinese Application No. 201710425696.6 mailed Nov. 4, 2019.
Office Action for Japanese Application No. 2017-184962 mailed Jul. 31, 2018.
Office Action for Japanese Application No. 2019/032726 mailed Feb. 18, 2020.
Office Action for Japanese Application No. 2019/032726 mailed Jan. 19, 2021.
Restriction Requirement for U.S. Appl. No. 13/475,994 mailed Mar. 11, 2014.
Translation Dated Dec. 28, 2015 of Notification of Office Action Dated Dec. 3, 2015 From the State Intellectual Property Office of the People's Republic of China Re. Application No. 201380038199.0.
Translation of Notification of Office Action and Search Report Dated Sep. 7, 2016 From the State Intellectual Property Office of the People's Republic of China Re. Application No. 201380038199.0.
U.S. Appl. No. 12/582,986, filed Oct. 21, 2009.
U.S. Appl. No. 14/402,387, filed Nov. 20, 2014.
U.S. Appl. No. 16/374,240, filed Apr. 3, 2019.
U.S. Appl. No. 61/649,319, filed May 20, 2012.
U.S. Appl. No. 62/767,018, filed Nov. 14, 2018.
U.S. Appl. No. 62/886,366, filed Aug. 14, 2019.
Applicant-Initiated Interview Summary for U.S. Appl. No. 14/402,387 mailed Dec. 28, 2017.
Applicant-Initiated Interview Summary for U.S. Appl. No. 14/402,387 mailed May 25, 2017.
Final Office Action for U.S. Appl. No. 13/083,643 mailed Mar. 5, 2014.
Final Office Action for U.S. Appl. No. 13/475,994 mailed Jun. 8, 2018.
International Search Report and Written Opinion from International Application No. PCT/IB2023/055160 mailed Jul. 28, 2023.
Issue Notification for U.S. Appl. No. 13/475,994 mailed Nov. 20, 2019.
Issue Notification for U.S. Appl. No. 16/655,656 mailed Feb. 1, 2023.
Issue Notification for U.S. Appl. No. 17/349,152 mailed Sep. 20, 2023.
Non-Final Office Action for U.S. Appl. No. 13/475,994 mailed Dec. 28, 2018.
Non-Final Office Action for U.S. Appl. No. 17/263,776 mailed Oct. 25, 2023.
Non-Final Office Action for U.S. Appl. No. 17/488,623 mailed Oct. 26, 2023.
Non-Final Office Action for U.S. Appl. No. 17/488,628 mailed Oct. 26, 2023.
Notice of Allowance for U.S. Appl. No. 13/475,994 mailed Jul. 22, 2019.
Notice of Allowance for U.S. Appl. No. 16/655,656 mailed Oct. 25, 2022.
Office Action for Japanese Application No. 2021-525788 mailed Nov. 1, 2023.
U.S. Appl. No. 13/475,994, filed May 20, 2012.
U.S. Appl. No. 16/655,656, filed Oct. 17, 2019.
U.S. Appl. No. 17/263,776, filed Jan. 27, 2021.
U.S. Appl. No. 18/103,671, filed Jan. 31, 2023.
U.S. Appl. No. 61/488,180 filed May 20, 2011.
U.S. Appl. No. 63/211,602, filed Jun. 17, 2021.
Examination Report for Indian Application No. 202170217772 mailed Jan. 11, 2023.
Hearing Notice for Indian Application No. 2424/MUMNP/2014 mailed Jan. 3, 2023.
International Search Report and Written Opinion from International Application No. PCT/IB2019/059734 mailed Jan. 30, 2020.
International Search Report and Written Opinion from International Application No. PCT/IB2022/054099 mailed Sep. 12, 2022.
International Search Report and Written Opinion from International Application No. PCT/IB2022/055593 mailed Nov. 14, 2022.
Invitation to Pay Additional Fees for International Application No. PCT/IB2022/054099 mailed Jul. 20, 2022.
Invitation to Pay Additional Fees for International Application No. PCT/IB2022/055593 mailed Sep. 23, 2022.
U.S. Appl. No. 17/349,152, filed Jun. 16, 2021.
U.S. Appl. No. 17/488,623, filed Sep. 29, 2021.

(56) References Cited

OTHER PUBLICATIONS

U.S. Appl. No. 17/488,628, filed Sep. 29, 2021.
U.S. Appl. No. 17/932,014, filed Sep. 14, 2022.
U.S. Appl. No. 63/184,403, filed May 5, 2021.
U.S. Appl. No. 63/184,427, filed May 5, 2021.
Communication Pursuant to Rule 94(3) for European Patent Application No. 20760551.0 mailed Apr. 7, 2022.
International Search Report and Written Opinion for International Application No. PCT/IB2021/059798 mailed Jan. 24, 2022.
International Search Report and Written Opinion for International Application No. PCT/IB2021/059799 mailed Jan. 25, 2022.
Issue Notification for U.S. Appl. No. 16/374,240 mailed Jun. 30, 2021.
Non-Final Office Action for U.S. Appl. No. 16/655,656 mailed Jun. 17, 2022.
Office Action for Japanese Application No. 2019/032726 mailed Nov. 19, 2021.
Final Office Action for U.S. Appl. No. 17/488,628 mailed Jul. 31, 2024.
Final Office Action for U.S. Appl. No. 18/103,671 mailed Jul. 29, 2024.
Non-Final Office Action for U.S. Appl. No. 17/488,623 mailed Jul. 31, 2024.
Examination Report for Indian Application No. 202247005897 mailed Dec. 11, 2024.
International Search Report and Written Opinion from International Application No. PCT/IB2024/052304 mailed Jun. 17, 2024.
Issue Notification for U.S. Appl. No. 17/488,628 mailed Oct. 23, 2024.
Issue Notification for U.S. Appl. No. 17/932,014 mailed Sep. 4, 2024.
Issue Notification for U.S. Appl. No. 18/103,671 mailed Jan. 8, 2025.
Notice of Allowance for U.S. Appl. No. 17/488,623 mailed Jan. 6, 2025.
Notice of Allowance for U.S. Appl. No. 18/103,671 mailed Sep. 28, 2024.
Office Action for Chinese Application No. 201980082413.X mailed Sep. 26, 2024.
Office Action for Israel Application No. 283093 mailed Jan. 16, 2025.
Office Action for Israel Application No. 290306 mailed Jul. 7, 2024.
U.S. Appl. No. 18/814,988, filed Aug. 26, 2024.
U.S. Appl. No. 18/867,696, filed Nov. 20, 2024.
U.S. Appl. No. 18/994,876, filed Jan. 15, 2025.
U.S. Appl. No. 18/999,207, filed Dec. 23, 2024.
U.S. Appl. No. 63/344,590, filed May 22, 2022.
U.S. Appl. No. 63/405,966, filed Sep. 13, 2022.
Examination Report for European Application No. 21801644.2 mailed May 2, 2024.
Final Office Action for U.S. Appl. No. 17/488,623 mailed May 30, 2024.
International Search Report and Written Opinion from International Application No. PCT/IB2023/059084 mailed Feb. 12, 2024.
Invitation to Pay Additional Fees for International Application No. PCT/IB2023/059084 mailed Dec. 22, 2023.
Non-Final Office Action for U.S. Appl. No. 17/488,628 mailed May 31, 2024.
Non-Final Office Action for U.S. Appl. No. 18/103,671 mailed Apr. 2, 2024.
Notice of Allowance for U.S. Appl. No. 17/263,776 mailed Apr. 9, 2024.
Notice of Allowance for U.S. Appl. No. 17/932,014 mailed May 22, 2024.
Office Action for Chinese Application No. 201980082413 mailed Jan. 31, 2024.
Office Action for Israel Application No. 283093 mailed Feb. 18, 2024.
Office Action for Japanese Application No. 2021-525788 mailed Mar. 11, 2024.
Office Action for Japanese Application No. 2022-508890 mailed Apr. 9, 2024.

* cited by examiner

FIG. 4 ately. During implantation of the annuloplasty ring, the arms are typically used to maintain the size of the valve annulus at its decreased size, by maintaining the arms
ATRIOVENTRICULAR VALVE REPAIR

CROSS-REFERENCES TO RELATED APPLICATIONS

The present application is a US national stage application of PCT Application No. PCT/IB2019/059734 to Raanani, filed Nov. 13, 2019, which claims priority from U.S. Provisional Patent Application 62/767,018 to Raanani, filed Nov. 14, 2018, entitled "Atrioventricular valve repair," the entire disclosure of each of which is incorporated herein by reference.

FIELD OF EMBODIMENTS OF THE INVENTION

The present invention relates to medical apparatus and methods, and specifically to apparatus and methods for repairing an atrioventricular valve.

BACKGROUND

The human heart is a muscular organ that pumps deoxygenated blood through the lungs to oxygenate the blood and pumps oxygenated blood to the rest of the body by contractions of four chambers.

After having circulated in the body, deoxygenated blood from the body enters the right atrium through the vena cava(s). In a healthy subject, the right atrium contracts, pumping the blood through the tricuspid valve into the right ventricle. The right ventricle contracts, pumping the blood through the pulmonary semi-lunar valve into the pulmonary artery which splits to two branches, one for each lung. The blood is oxygenated while passing through the lungs, and reenters the heart via the left atrium. The left atrium contracts, pumping the oxygenated blood through the mitral valve into the left ventricle. The left ventricle contracts, pumping the oxygenated blood through the aortic valve into the aorta to be distributed to the rest of the body. The tricuspid valve closes during right ventricle contraction, so that backflow of blood into the right atrium is prevented. Similarly, the mitral valve closes during left ventricle contraction, so that backflow of blood into the left atrium is prevented. The mitral valve and the tricuspid valve are known as atrioventricular valves, each of these valves controlling the flow of blood between an atrium and a ventricle.

In the mitral valve, the mitral annulus defines a mitral valve orifice. An anterior leaflet and a posterior leaflet extend from the mitral annulus. The leaflets are connected by chords to papillary muscles within the left ventricle.

During ventricular diastole, in a healthy subject, the left atrium contracts to pump blood into the left ventricle through the mitral valve orifice. The blood flows through the orifice, pushing the leaflets apart and into the left ventricle with minimal resistance. In a healthy subject, the leaflets of the aortic valve are kept closed by blood pressure in the aorta.

During ventricular systole, the left ventricle contracts to pump blood into the aorta through the aortic valve, the leaflets of which are pushed open by the blood flow. In a healthy subject, the mitral annulus contracts, pushing the leaflets inwards and reducing the area of the mitral valve orifice by about 20% to 30%. The leaflets coapt to accommodate the excess leaflet surface area, producing a coaptation surface that constitutes a seal. The pressure of blood in the left ventricle pushes against the ventricular surfaces of the leaflets, tightly pressing the leaflets together at the coaptation surface so that a tight, leak-proof seal is formed.

An effective seal of the mitral valve during ventricular systole depends on a sufficient depth of coaptation. Improper coaptation may be caused by any number of physical anomalies that allow leaflet prolapse (for example, elongated or ruptured chords, or weak papillary muscles) or prevent coaptation (for example, short chords, or small leaflets). There are also pathologies that lead to a mitral valve insufficiency, including collagen vascular disease, ischemic mitral regurgitation (resulting, for example, from myocardial infarction, chronic heart failure, or failed/unsuccessful surgical or catheter revascularization), myxomatous degeneration of the leaflets, and rheumatic heart disease. Mitral valve regurgitation leads to many complications including arrhythmia, atrial fibrillation, cardiac palpitations, chest pain, congestive heart failure, fainting, fatigue, low cardiac output, orthopnea, paroxysmal nocturnal dyspnea, pulmonary edema, shortness of breath, and sudden death.

The tricuspid valve includes three leaflets: the septal leaflet, the anterior leaflet, and the posterior leaflet. Each of the valve leaflets is attached to the tricuspid valve annulus, which defines the tricuspid valve orifice. The leaflets are connected to papillary muscles within the right ventricle, by chords. In a healthy subject the tricuspid valve controls the direction of blood flow from the right atrium to the right ventricle, in a similar manner to the control of the mitral valve over the direction of blood flow on the left side of the heart. During ventricular diastole, the tricuspid valve opens, such as to allow the flow of blood from the right atrium to the right ventricle, and during ventricular systole the leaflets of the tricuspid valve coapt, such as to prevent the backflow of blood from the right ventricle to the right atrium.

Tricuspid valve regurgitation occurs when the tricuspid valve fails to close properly. This can cause blood to flow back up into the right atrium when the right ventricle contracts. Tricuspid valve regurgitation is most commonly caused by right ventricle dilation, which leads to the tricuspid valve annulus dilating, resulting in the valve leaflets failing to coapt properly.

Apart from humans, mammals that suffer from mitral valve regurgitation and tricuspid valve regurgitation include horses, cats, dogs, cows, sheep and pigs.

It is known to use open-heart surgical methods to treat mitral valve regurgitation and tricuspid valve regurgitation, for example, by modifying the subvalvular apparatus (for example, lengthening or shortening chords) to improve leaflet coaptation, and/or by implanting an annuloplasty ring to reduce the size of the valve annulus.

SUMMARY OF EMBODIMENTS

In accordance with some applications of the present invention, apparatus and methods are provided for facilitating the implantation of an annuloplasty ring on an atrioventricular valve of a subject's heart (e.g., the subject's mitral valve, or the subject's tricuspid valve). Typically, a plurality of chord-manipulation arms are deployed among chords of the atrioventricular valve. Subsequently the arms are rotated, such that the arms cause the size of the valve annulus to decrease, by the arms twisting the native atrioventricular valve and pulling the native atrioventricular valve radially inwards, by deflecting the chords. Subsequent to the arms having been rotated, the annuloplasty ring is implanted upon the valve annulus. During implantation of the annuloplasty ring, the arms are typically used to maintain the size of the valve annulus at its decreased size, by maintaining the arms in their rotated state. For some applications, during implantation of the annuloplasty ring, the arms are used to provide a counterforce against which the annuloplasty ring is pushed, by pulling the arms from beneath the valve leaflets toward the annuloplasty ring.

Typically, subsequent to the annuloplasty ring having been implanted, the chord-manipulation arms are rotated in the opposite direction to the direction in which they were previously rotated and the arms are removed from the subject's body. Typically, the rotation of the chord-manipulation in the opposite direction allows the native atrioventricular valve to become untwisted. However, the annuloplasty ring maintains the atrioventricular valve annulus at a reduced size relative to the dilated size of the annulus prior to the implantation of the ring. For some applications, the annuloplasty ring is anchored to arms, portions of the arms, and/or extensions from the arms, and the arms, portions thereof, and/or extensions therefrom are left in place under the atrioventricular valve leaflets. For some applications, portions of the arms, and/or extensions from the arms are configured to be detachable and to be left in place under the atrioventricular valve leaflets, even after the arms or portions thereof are removed from the subject's ventricle.

There is therefore provided, in accordance with some applications of the present invention, apparatus for use with an annuloplasty ring, and an atrioventricular valve of a heart of a mammalian subject, the atrioventricular valve including a valve annulus, valve leaflets, chords, and papillary muscles, the apparatus including:

a plurality of chord-manipulation arms configured:
to be deployed among the chords of the atrioventricular valve;
subsequently cause the size of the valve annulus to decrease, by the chord-manipulation arms being rotated such as to twist the native atrioventricular valve and pull the native atrioventricular valve radially inwards, by the chord-manipulation arms deflecting the chords; and
subsequently to provide a counterforce against which the annuloplasty ring is pushed, during implantation of the annuloplasty ring.

In some applications, the chord-manipulation arms are configured, subsequent to the annuloplasty ring having been implanted, to allow the native atrioventricular valve to become untwisted by the chord-manipulation arms being rotated in an opposite direction to the direction of the rotation of the chord-manipulation arms that caused the native atrioventricular valve to become twisted.

In some applications, the apparatus further includes the annuloplasty ring.

In some applications, the atrioventricular valve includes a mitral valve, and the chord-manipulation arms are configured to be deployed among chords of the mitral valve. In some applications, the atrioventricular valve includes a tricuspid valve, and the chord-manipulation arms are configured to be deployed among chords of the tricuspid valve.

In some applications, the plurality of chord-manipulation arms include more than two chord-manipulation arms and fewer than 12 chord-manipulation arms.

In some applications, the chord-manipulation arms are sized such that, when disposed in radially-non-constrained configurations, the chord-manipulation arms span a diameter that is at least equal to an inner diameter of the annuloplasty ring, such that the chord-manipulation arms are configured to provide a counterforce against which the annuloplasty ring may be pushed, during implantation of the annuloplasty ring. In some applications, the chord-manipulation arms are sized such that, when disposed in radially-non-constrained configurations, the chord-manipulation arms are configured to overlap radially with the annuloplasty ring, such that the chord-manipulation arms are configured to provide a counterforce against which the annuloplasty ring may be pushed, during implantation of the annuloplasty ring.

In some applications, at least a portion of an inner edge of each of the chord-manipulation arms is concavely curved in a given circumferential direction, and the chord-manipulation arms are configured to pull the native atrioventricular valve radially inwards by being rotated in the given circumferential direction. In some applications, the inner edge of each of the chord-manipulation arms is concavely curved in the given circumferential direction along the entire length of the inner edge of the chord-manipulation arm. In some applications, a radially outermost portion of the inner edge of each of the chord-manipulation arms is concavely curved in the given circumferential direction.

In some applications, the chord-manipulation arms, portions thereof, and/or extensions from the chord-manipulation arms are configured to be left under the atrioventricular valve leaflets and the annuloplasty ring is configured to become anchored to the chord-manipulation arms, portions thereof, and/or extensions from the chord-manipulation arms. In some applications, the chord-manipulation arms include first and second portions, the annuloplasty ring is configured to become anchored to the first portions of the chord-manipulation arms, and the first portions of the chord-manipulation arms are configured to be detachable from the second portions of the chord-manipulation arms, and are configured to be left under the atrioventricular valve leaflets, even after the second portions of the chord-manipulation arms are removed from the subject's ventricle. In some applications, the annuloplasty ring is configured to become anchored to extensions from the chord-manipulation arms, and the extensions from the chord-manipulation arms are configured to be detachable and to be left under the atrioventricular valve leaflets, even after the chord-manipulation arms are removed from the subject's ventricle. In some applications, plates are disposed at the ends of at least some of the chord-manipulation arms, the plates being configured to be left under the atrioventricular valve leaflets, and the annuloplasty ring is configured to become anchored to the plates. In some applications, the annuloplasty ring includes a plurality of anchoring elements, and at least some of the anchoring elements are configured to become embedded in the chord-manipulation arms, portions thereof, and/or extensions from the chord-manipulation arms.

In some applications, the apparatus further includes a frame configured to extend from below the atrioventricular valve leaflets into an atrium of the subject's heart, the frame defining holes which are sized such as to allow blood to flow from the atrium to a ventricle of the subject's heart via the frame, and the chord-manipulation arms are coupled to a portion of the frame that is configured to be disposed within the ventricle. In some applications, the portion of the frame that is configured to be disposed within the ventricle is configured to radially self-expand such that the location upon the frame to which the arms are coupled has a greater circumference than a portion of the frame that is configured to be disposed within the atrium.

In some applications,
the apparatus further includes a support rod and a hollow tube that define holes,
the chord-manipulation arms are coupled to the support rod and the support rod is configured to be disposed inside the hollow tube, and the holes within the hollow tube are sized such as to allow blood to flow from an atrium of the subject's heart to a ventricle of the subject's heart via the hollow tube.

In some applications, the apparatus further includes a unidirectional valve disposed within the hollow tube, and configured to allow blood flow from the atrium to the ventricle, but to block blood flow in the opposite direction.

In some applications, the apparatus further includes a delivery device configured to deliver the chord-manipulation arms to a ventricle of the subject's heart, the arms are disposed at an angle of between 45 degrees and 135 degrees with respect to a longitudinal axis of a distal-most portion of the delivery device. In some applications, the arms are disposed at an angle of between 70 degrees and 110 degrees with respect to the longitudinal axis of the distal-most portion of the delivery device. In some applications, the arms are disposed at an angle of between 85 degrees and 95 degrees with respect to the longitudinal axis of the distal-most portion of the delivery device. In some applications, the arms are disposed at an angle of approximately 90 degrees with respect to the longitudinal axis of the distal-most portion of the delivery device.

In some applications, the apparatus further includes a plurality of support elements, each of the chord-manipulation arms is coupled to a respective one of the support elements, during delivery of the arms to a ventricle of the subject's heart, the support elements are configured to be held together with each other, and, during deployment of the arms inside the ventricle, the support elements are configured to be separated from each other. In some applications, the apparatus further includes a separation element, and the support elements are configured to be separated from each other by retracting the separation element such that it is disposed between the support elements. In some applications, the support elements are configured to allow blood flow from an atrium of the subject's heart to the ventricle, by becoming separated from each other.

There is further provided, in accordance with some applications of the present invention, apparatus for use an atrioventricular valve of a heart of a mammalian subject, the atrioventricular valve including a valve annulus, valve leaflets, chords, and papillary muscles, the apparatus including:
an annuloplasty ring that defines an inner diameter; and
a plurality of arms that are sized such that, when disposed in radially-non-constrained configurations, the arms span a diameter that is at least equal to the inner diameter of the annuloplasty ring, such that the arms are configured to provide a counterforce against which the annuloplasty ring is pushed, during implantation of the annuloplasty ring.

There is further provided, in accordance with some applications of the present invention, a method for use with an annuloplasty ring, and an atrioventricular valve of a heart of a mammalian subject, the atrioventricular valve including a valve annulus, valve leaflets, chords, and papillary muscles, the method including:
deploying a plurality of chord-manipulation arms among the chords of the atrioventricular valve;
subsequently rotating the arms, such that the arms cause the size of the valve annulus to decrease, by the arms twisting the native atrioventricular valve and pulling the native atrioventricular valve radially inwards, by deflecting the chords; and
subsequently, implanting the annuloplasty ring on the valve annulus, while using the arms (a) to maintain the size of the valve annulus at its decreased size, by maintaining the arms in their rotated state, and (b) to provide a counterforce against which the annuloplasty ring is pushed, by pulling the arms from beneath the valve leaflets toward the annuloplasty ring.

There is further provided, in accordance with some applications of the present invention, a method for use with an annuloplasty ring, and an atrioventricular valve of a heart of a mammalian subject, the atrioventricular valve including a valve annulus, valve leaflets, chords, and papillary muscles, the method including:
deploying a plurality of arms below leaflets of the native atrioventricular valve; and
subsequently, implanting the annuloplasty ring on the valve annulus, while using the arms to provide a counterforce against which the annuloplasty ring is pushed, by pulling the arms from beneath the valve leaflets toward the annuloplasty ring.

The present invention will be more fully understood from the following detailed description of applications thereof, taken together with the drawings, in which:

DETAILED DESCRIPTION OF EMBODIMENTS

Reference is now made to FIGS. 1A, 1B, 1C, 1D, and 1E, which are schematic illustrations of respective steps of a procedure for implanting an annuloplasty ring 20 (shown in FIGS. 1C-E) on an atrioventricular valve 22 of a subject, in accordance with some applications of the present invention. The atrioventricular valve separates between an atrium 16 and a ventricle 18, and typically includes a valve annulus 21, valve leaflets 23, chords 25, and papillary muscles 27.

Figure 1A:
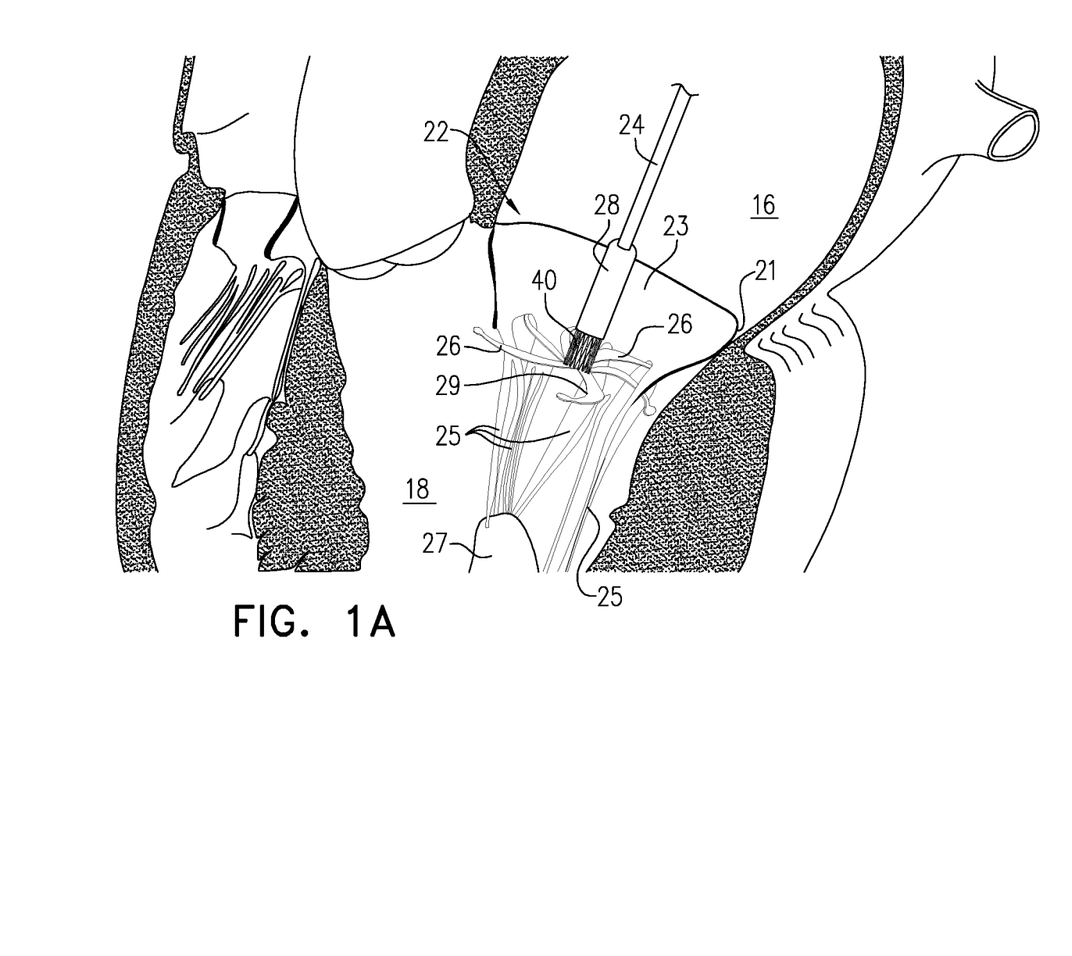
FIGS. 1A, 1B, 1C, 1D, and 1E are schematic illustrations of respective steps of a procedure for implanting an annuloplasty ring on an atrioventricular valve of a subject, in accordance with some applications of the present invention.

In a first step of the procedure, a delivery device 24 is delivered to the atrioventricular valve. A plurality of chord-manipulation arms 26 are then released from the delivery device, as shown in FIG. 1A. It is noted that in FIGS. 1A-1G and in FIG. 5, chord-manipulation arms 26 are shown as being deployed among chords of the mitral valve. However the scope of the present application includes applying the apparatus and methods described herein to the tricuspid valve, mutatis mutandis. It is further noted that in FIGS. 1A-1D, FIG. 1F and FIG. 5, the delivery device is shown as being introduced from above the mitral valve (e.g., via transseptal or transatrial delivery). However, the scope of the present application includes introducing the delivery device from underneath the mitral valve (e.g., via transapical delivery). For applications in which the apparatus and methods described herein are applied to the tricuspid valve, the delivery device is typically delivered to the tricuspid valve via a jugular vein, a subclavian vein, or the inferior vena cava. Finally, it is noted that, for illustrative purposes, in FIGS. 1A-D and in FIG. 5 of the present application, a cross-sectional view is shown of the heart (and of the annuloplasty ring, where relevant), in combination with a full three-dimensional view of chord-manipulation arms 26.

For some applications, a covering sheath 28 of the delivery device is retracted with respect to chord-manipulation arms 26 or the arms are pushed forward relative to the delivery device, in order to release the arms from the delivery device. Typically, the arms are made of a shape memory material (e.g., a shape memory alloy, such as nitinol or copper-aluminum-nickel) that is shape set such that, upon being released from the delivery device, the arms extend radially outwardly with respect to the delivery device. Alternatively, the arms are made of a different material. The arms are typically configured to extend radially outwardly to a sufficient extent for the arms to become deployed among chords 25 of the atrioventricular valve, as shown in FIG. 1A. For some applications, the arms extend radially outwardly to a sufficient extent for the arms to become deployed among primary chords, and/or secondary chords. Further typically, the arms are shape set such that the arms are circumferentially curved, as shown. For some applications, the circumferential curvature each of the arms is such that at least a portion of an inner edge 29 (shown in FIG. 1A) of the arm is concavely curved in a given circumferential direction. For example, as shown in FIG. 1A, at least a portion of inner edge 29 of the arm is concavely curved in the clockwise circumferential direction. For some applications, inner edge 29 of the arm is concavely curved in the given circumferential direction along the entire length of the arm. Typically, at least the leading portion of inner edge 29 of the arm (i.e., the radially outermost portion of the inner edge of the arm, which typically first encounters the chords) is concavely curved in the given circumferential direction.

Figure 1B:
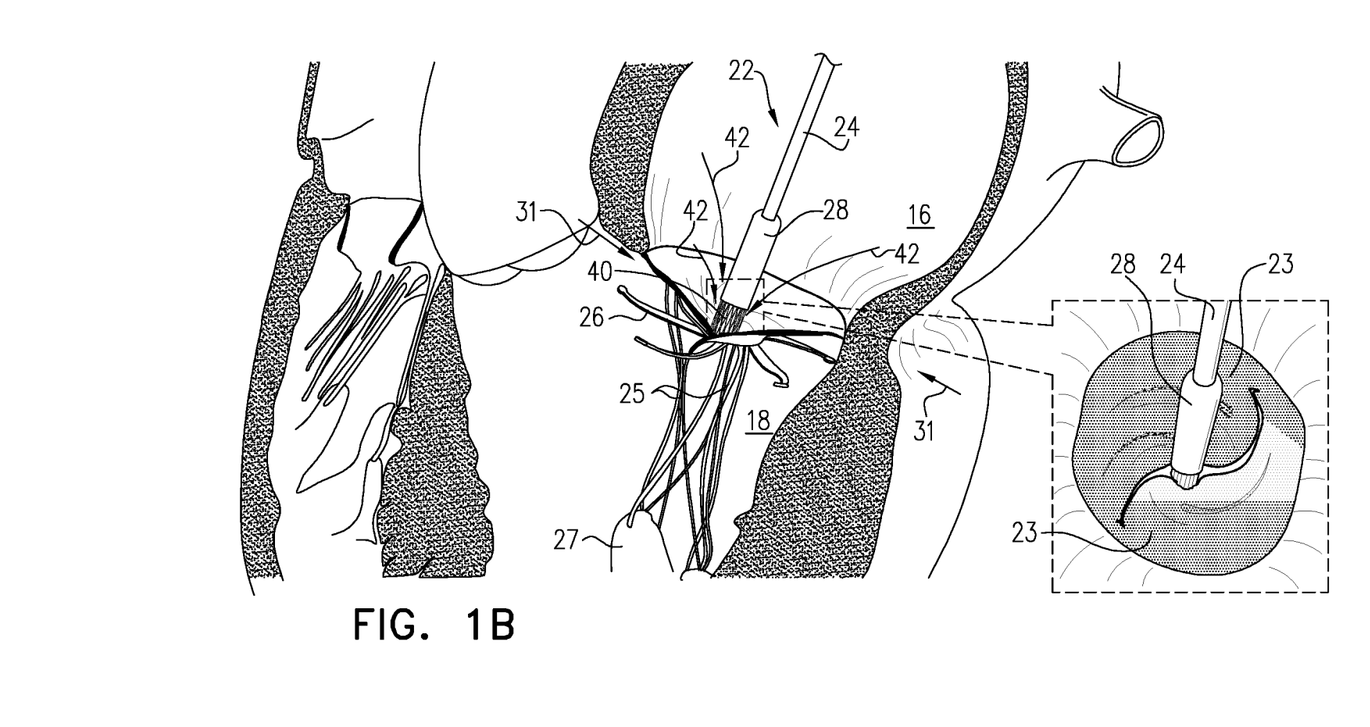

In a subsequent step of the procedure, chord-manipulation arms 26 are rotated (clockwise or counterclockwise) in the direction of the concave circumferential curvature of the inner edges of the arms. For example, for arms that are shaped as shown in FIG. 1A, the arms are rotated in the clockwise direction. Alternatively (not shown), the arms may be shaped such that concave circumferential curvature of the inner edges of the arms is in the counterclockwise direction, in which case the arms are typically rotated in the counterclockwise direction. Typically, the rotation of the arms causes chords among which the arms are deployed to become deflected. In turn, the deflection of the chords causes at least a portion of the atrioventricular valve (e.g., leaflets, and the annulus of the atrioventricular valve) to become twisted and pulled radially inwards toward the bases of the arms. This is because the chords extend between the papillary muscles at their first ends, and to the mitral annulus, via the leaflets, at their second ends. The deflection of the chords pulls the native atrioventricular valve radially inwards, thereby providing annular reduction. Thus, in this manner, atrioventricular valve annulus 21 becomes reduced in size relative to the size of the atrioventricular valve annulus prior to the rotation of the arms. FIG. 1B is a schematic illustration of the mitral valve after the arms have been rotated in the above-described manner. FIG. 1B includes a view (in the dashed box) from on top of the mitral valve. As shown, the valve leaflets have become twisted, due to the rotation of the arms. In addition, as may be noted by comparing FIG. 1B to FIG. 1A, the mitral valve annulus has been pulled radially inwards, in the direction of arrows 31, due to the rotation of the arms.

In a subsequent step of the procedure, annuloplasty ring 20 is implanted onto the atrioventricular valve annulus. During the implantation of the annuloplasty ring, the arms are maintained in their rotated state such that the arms maintain the atrioventricular valve annulus at its reduced size. In this manner the annuloplasty ring is implanted onto an atrioventricular valve annulus that is already reduced in size relative to its size prior to the initiation of the annuloplasty procedure. This is in contrast to some other techniques for implanting annuloplasty rings, in which the annulus is not reduced in size prior to the implantation of the annuloplasty ring. Rather, in accordance with such techniques, either the annuloplasty ring itself is used to reduce the size of the atrioventricular valve annulus during the implantation of the annuloplasty ring, and/or the ring is first attached to the atrioventricular valve annulus, and subsequently the diameter of the ring is reduced (e.g., by cinching the ring).

Figure 1C:
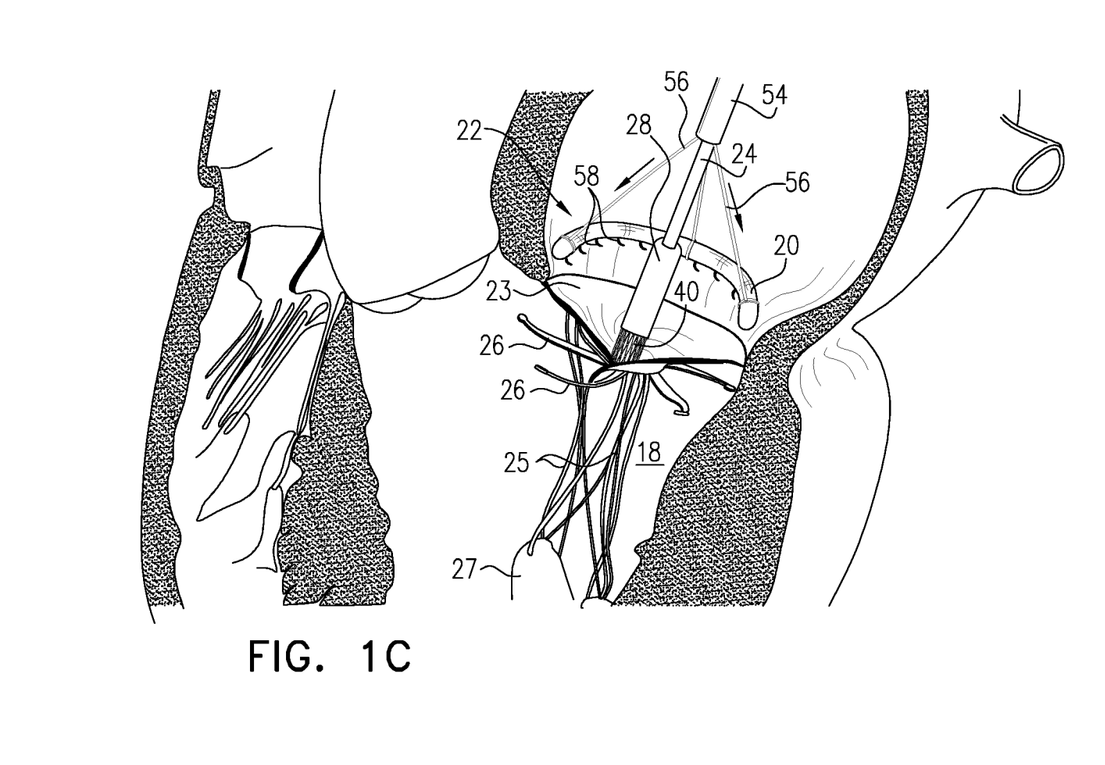
Figures 1D, 1E:
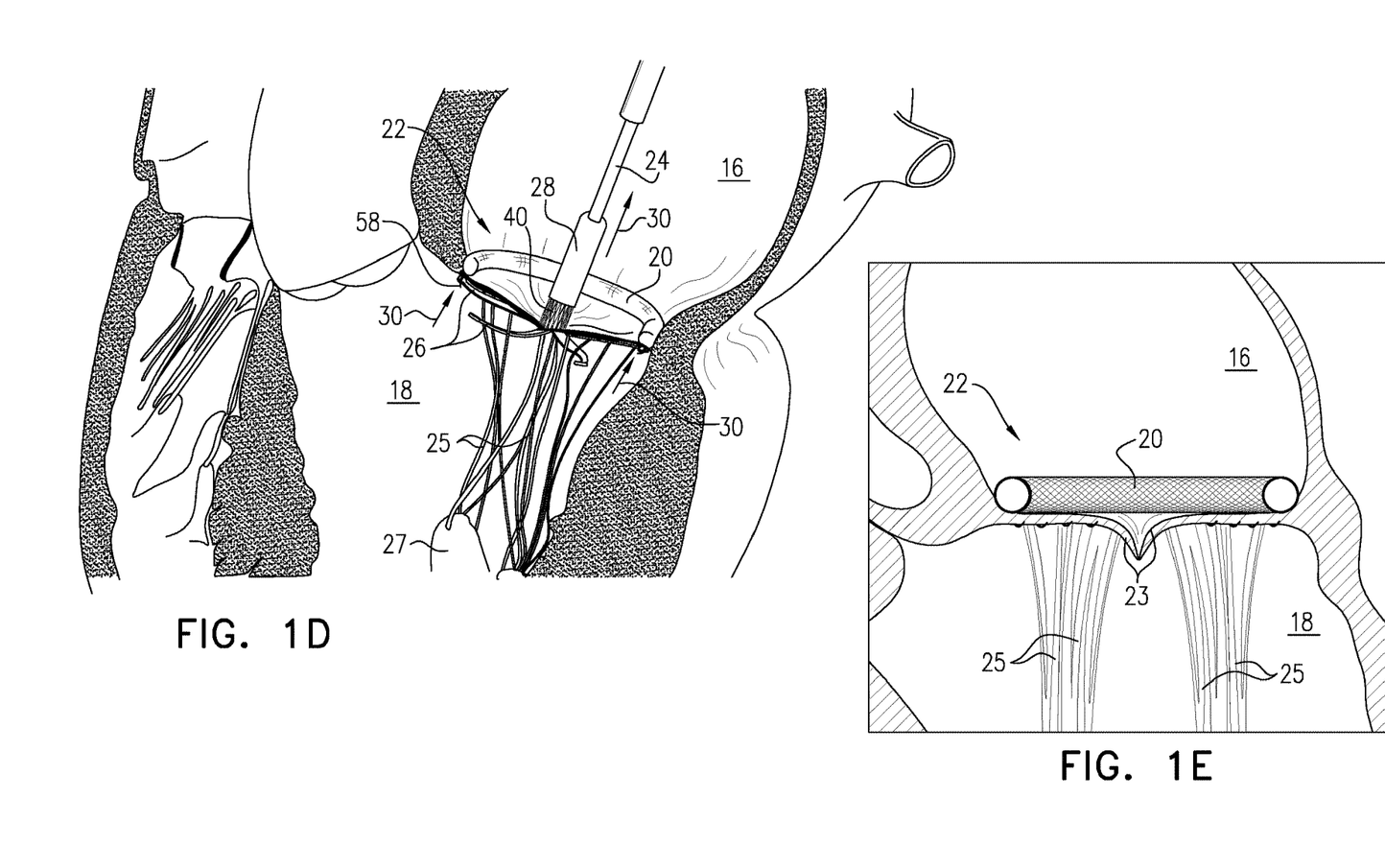

FIGS. 1C and 1D show the annuloplasty ring being delivered to the atrial side of the atrioventricular valve, using an annuloplasty ring delivery device 54 that is couplable to (or coupled to) delivery device 24, e.g., via elongate elements 56. For some applications, the annuloplasty ring includes a plurality of anchoring elements 58 (e.g., barbs, hooks, and/or other anchoring elements) that are configured to anchor the annuloplasty ring to the valve annulus, by becoming embedded in tissue of the annulus. For some applications, during the implantation of the annuloplasty ring, arms 26 are pulled toward the annuloplasty ring, such that the arms (which are disposed under the valve leaflets) provide a counterforce against which the annuloplasty ring is pushed (from above the valve leaflets), as indicated by arrows 30 in FIG. 1D. Typically, for such applications, the arms are sized such that, when disposed in radially-non-constrained configurations, the arms span a diameter that is at least equal to the inner diameter of the annuloplasty ring. Thus, the arms are configured such that, in their radially-non-constrained configurations, the arms overlap radially with the annuloplasty ring.

For some applications, subsequent to the annuloplasty ring being implanted, arms 26 are retracted into the delivery device, and are extracted from the subject's body, as shown in FIG. 1E, which shows a cross-sectional view of the implanted annuloplasty ring in the absence of the arms and the delivery device. At this stage, the annuloplasty ring typically holds the annulus in a reduced size (relative to its dilated size before the procedure). Typically, subsequent to the annuloplasty ring having been implanted, the chord-manipulation arms are rotated in the opposite direction to the direction in which they were previously rotated and the arms are removed from the subject's body. Typically, the rotation of the chord-manipulation in the opposite direction allows the native atrioventricular valve to become untwisted. However, the annuloplasty ring maintains the valve annulus at a reduced size relative to the dilated size of the annulus, prior to the implantation of the ring.

Figure 1F:
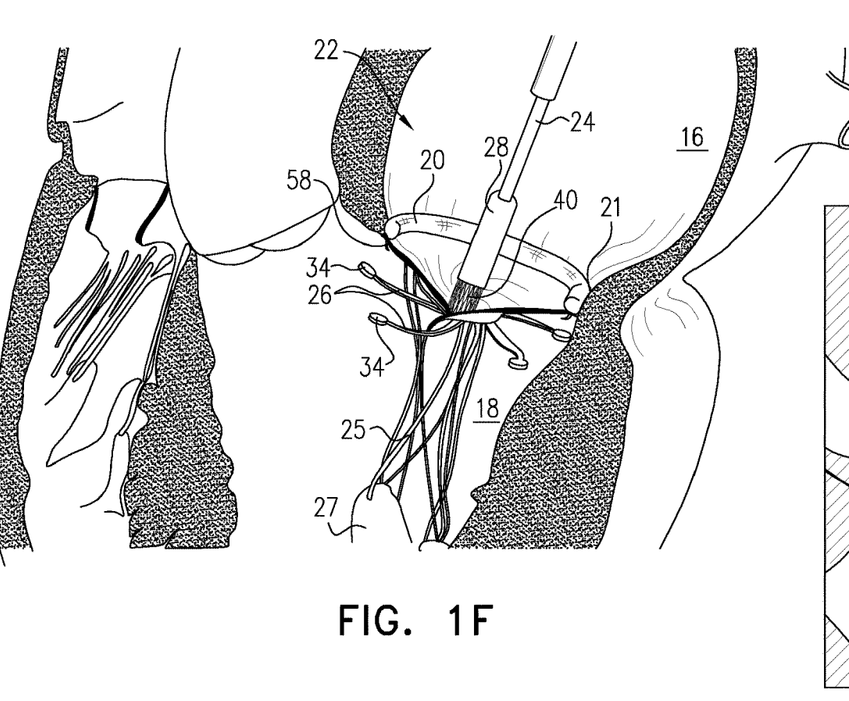
FIGS. 1F and 1G are schematic illustrations of the final steps of a procedure for implanting an annuloplasty ring on an atrioventricular valve of a subject, in which a portion of a device is implanted below the atrioventricular valve leaflets within the subject's ventricle, in accordance with some applications of the present invention.
Figure 1G:
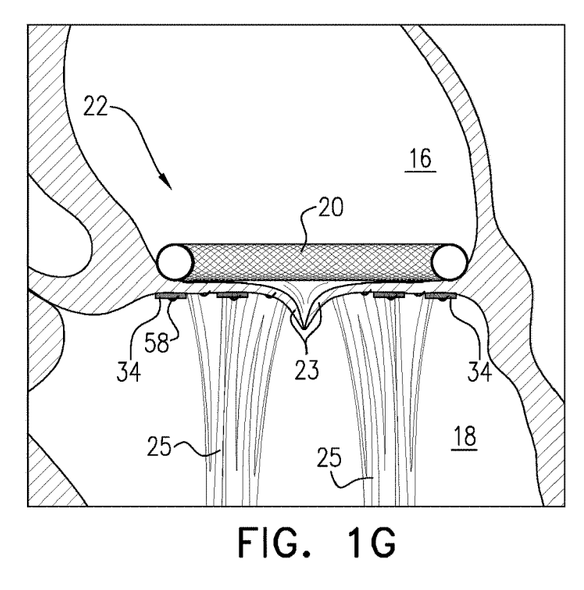

For some applications, the annuloplasty ring is anchored to arms 26, portions of the arms, and/or extensions from the arms, and the arms, portions thereof, and/or extensions therefrom are left in place under the atrioventricular valve leaflets, in order to provide the aforementioned anchoring function. For some applications, portions of the arms, and/or extensions from the arms are configured to be detachable and to be left in place under the atrioventricular valve leaflets, even after the arms or portions thereof are removed from the subject's ventricle. For example, FIGS. 1F and 1G show an embodiment in which plates 34 are disposed at the ends of the arms, and the annuloplasty ring becomes anchored to the plates (e.g., by at least some of anchoring elements 58 becoming embedded within the plates, as shown in FIG. 1G). In this manner, at least a portion of arms 26 and/or an extension of the arms functions as an intraventricular anchoring portion, to which the annuloplasty ring becomes anchored.

Figure 2A:
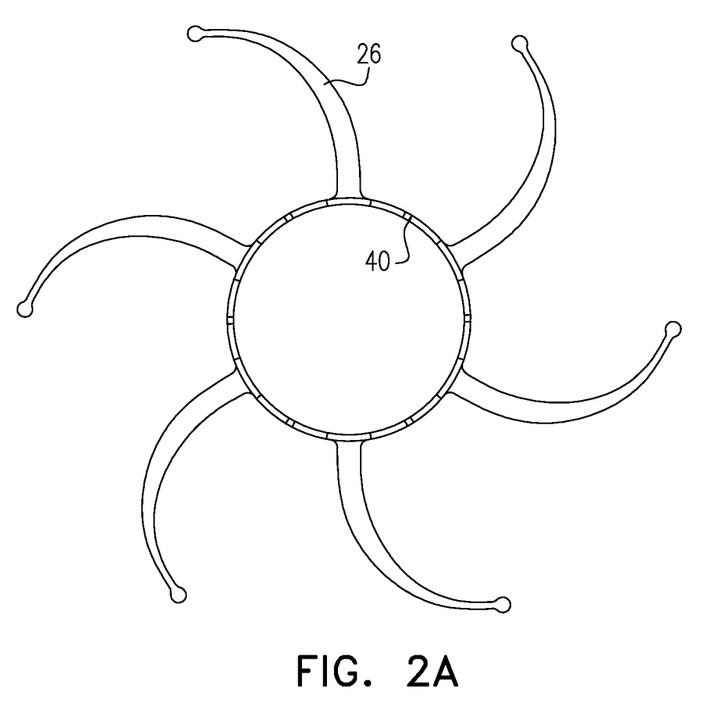
FIGS. 2A and 2B are schematic illustrations of respective views of a set of chord-manipulation arms that are used during the implantation of an annuloplasty ring on an atrioventricular valve of a subject, in accordance with some applications of the present invention.
Figure 2B:
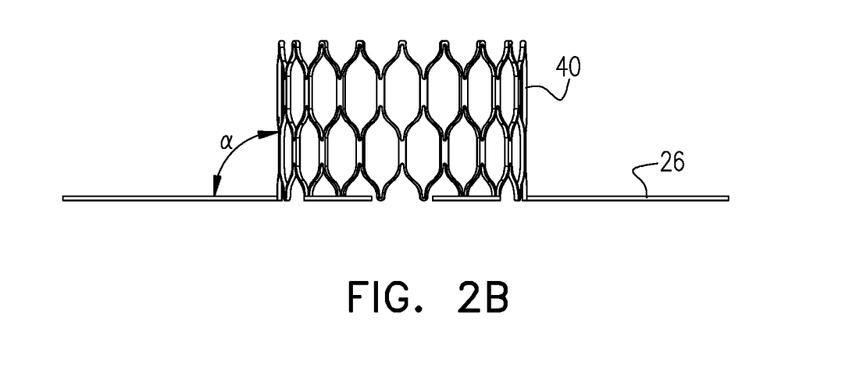

Reference is now made to FIGS. 2A and 2B, which are schematic illustrations of, respectively, a side view and a bottom view of a set of chord-manipulation arms 26 that are used during the implantation of annuloplasty ring 20 on an atrioventricular valve of a subject, in accordance with some applications of the present invention. For some applications, the arms are coupled to a frame 40 that is configured to extend from below the atrioventricular valve leaflets (i.e., within the ventricle) into the subject's atrium (e.g., as shown in FIGS. 1A-D, and 1F). The frame defines holes which are sized such as to allow blood to flow from the atrium to the ventricle via the frame, while the above-described procedure is being performed. This is indicated by arrows 42 indicating blood flow in FIG. 1B.

Figure 3:
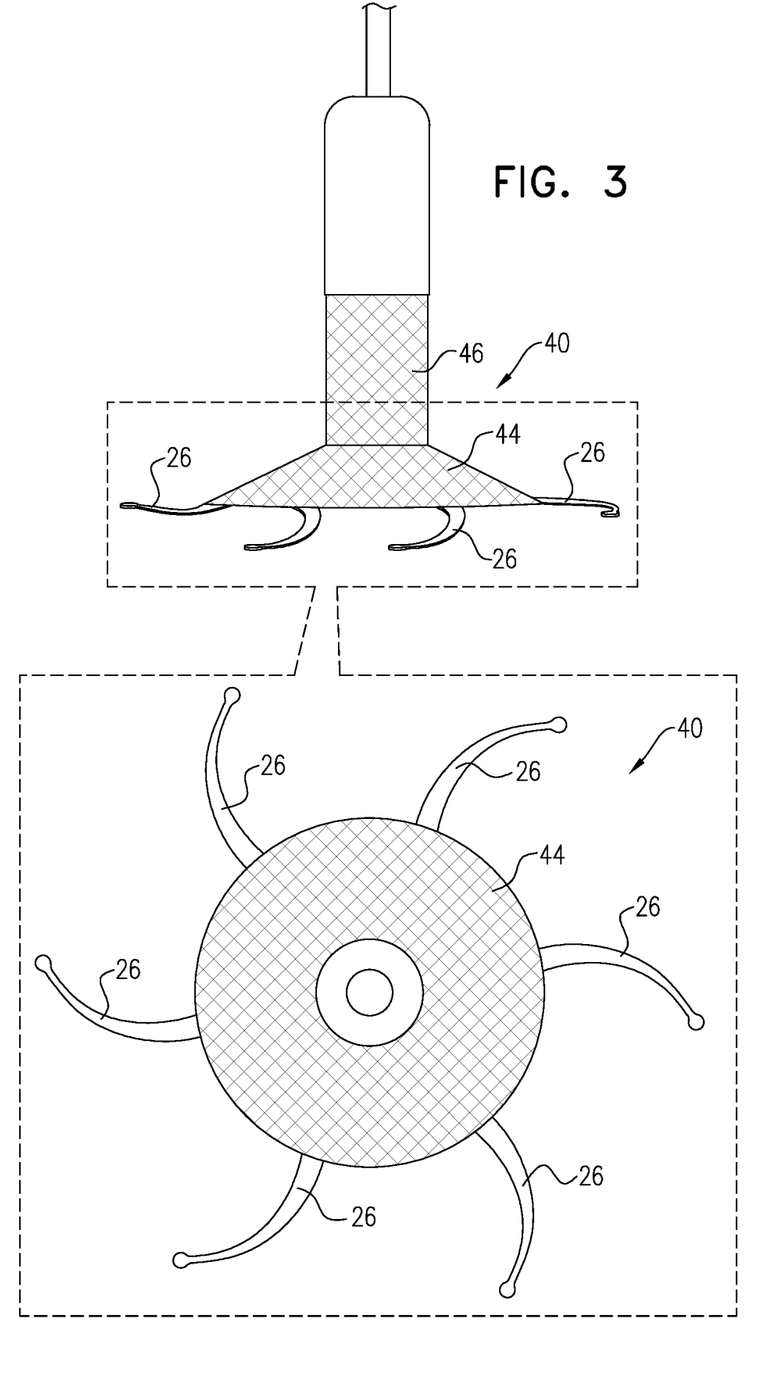
FIG. 3 is a schematic illustration of chord-manipulation arms attached to a frame that includes at least a ventricular portion that is radially self-expandable, in accordance with some applications of the present invention.

Reference is now made to FIG. 3, which is a schematic illustration of chord-manipulation arms 26 attached to frame 40. The arms are typically coupled to a ventricular portion 44 of the frame, and an atrial portion 46 of the frame extends upwards into the atrium, such as to facilitate blood flow from the atrium to the ventricle in the above-described manner. For some applications, ventricular portion 44 of the frame is configured to radially self-expand such that the location upon the frame to which the arms are coupled has a greater circumference than the atrial portion of the frame. For some applications, the expansion of the ventricular portion of the frame facilitates extension of the arms radially outwardly to a sufficient extent for the arms to become deployed among chords 25 (e.g., primary chords, and/or secondary chords) of the atrioventricular valve.

Figure 4:
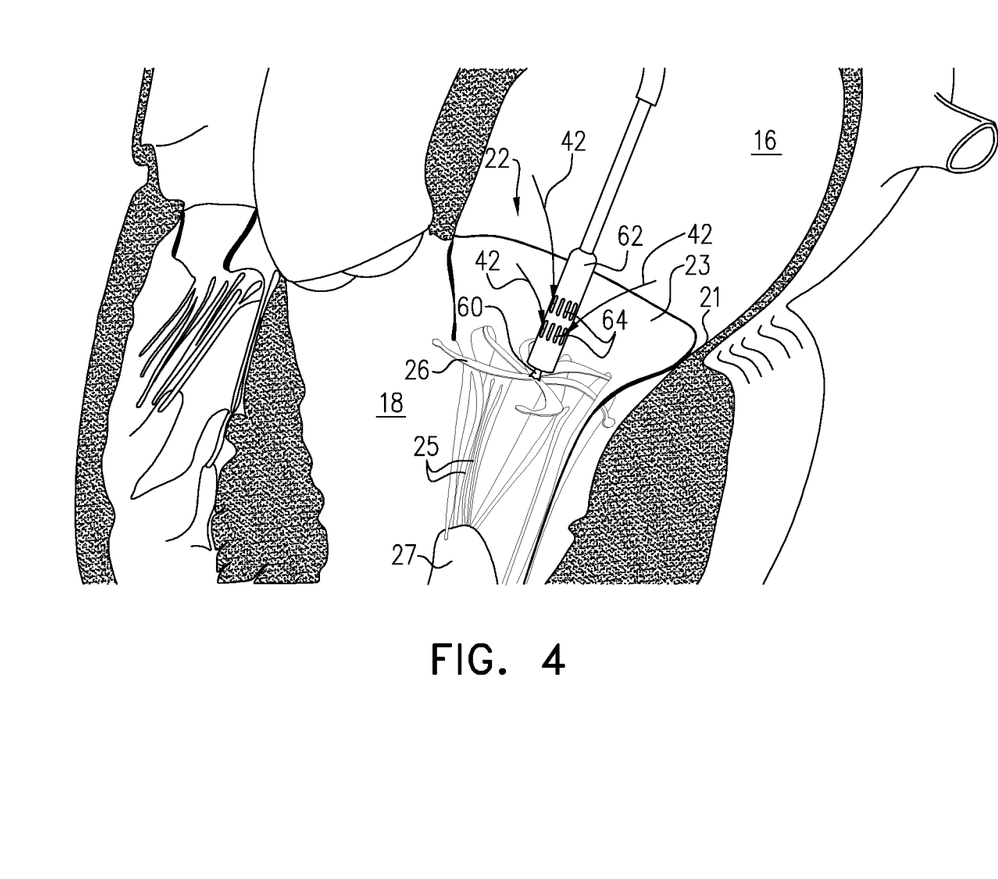
FIG. 4 is a schematic illustration of chord-manipulation arms coupled to a support rod, in accordance with some applications of the present invention.

Reference is now made to FIG. 4, which is a schematic illustration of chord-manipulation arms 26 coupled to a support rod 60, in accordance with some applications of the present invention. Typically, support rod 60 is disposed inside a hollow tube 62, the hollow tube defining holes 64 (e.g., lateral holes, as shown) that are configured to be disposed within the atrium. The holes are sized such as to allow blood to flow from the atrium to the ventricle via the hollow tube (as indicated by blood flow arrows 42), and out of an outflow hole disposed within the ventricle (from which the arms typically protrude). The holes through hollow tube 62 typically allow blood to flow from the atrium to the ventricle, while the above-described procedure is being performed. For some applications, a unidirectional valve (not shown) is disposed within hollow tube 62. The unidirectional valve is configured to allow blood flow from the atrium to the ventricle, but to block the flow of blood in the opposite direction.

Referring again to FIG. 2B, for some applications, an angle "alpha" that the arms make with respect to frame 40 or support rod 60 (and make with respect to the longitudinal axis of the distal-most portion of the delivery device) is approximately 90 degrees (e.g. 90 degrees plus/minus 3 degrees, or exactly 90 degrees). Alternatively, the angle may be an acute or an obtuse angle. For some applications, the arms are disposed at an angle alpha of 45-135 degrees (e.g., 70-110 degrees, or 85-95 degrees) with respect to the longitudinal axis of the distal-most portion of the delivery device.

Figure 5A:
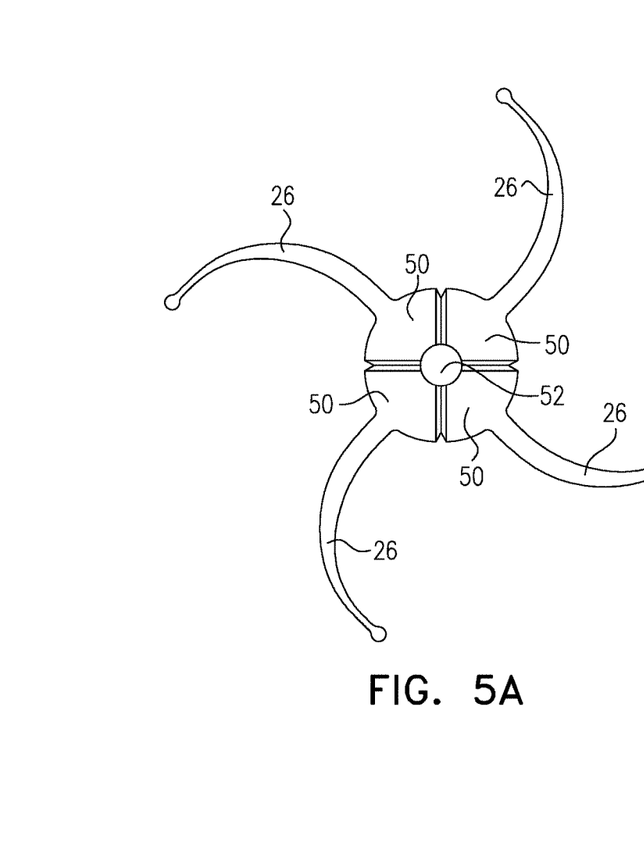
FIGS. 5A, 5B, and 5C are schematic illustrations of respective views of a set of chord-manipulation arms that are used during the implantation of an annuloplasty ring on an atrioventricular valve of a subject, in accordance with some applications of the present invention.
Figure 5B:
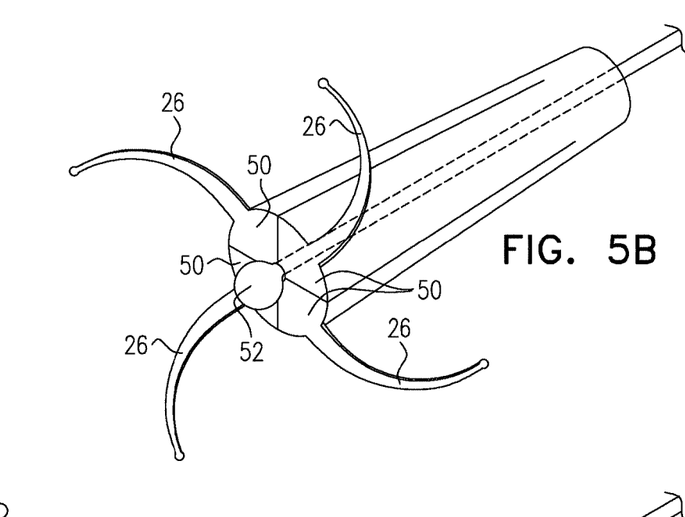
Figure 5C:
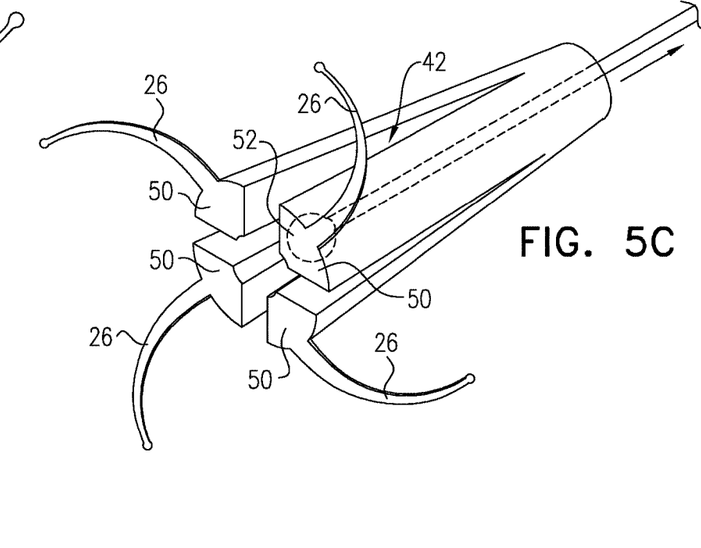

Reference is now made to FIGS. 5A and 5B, which are schematic illustrations of respective views of a set of chord-manipulation arms 26 that are used during the implantation of annuloplasty ring 20 on an atrioventricular valve of a subject, in accordance with some applications of the present invention. For some applications, each of the arms is coupled to a respective support element 50, and the support elements are separable from each other. During delivery of the arms to the ventricle, the support elements are typically held together with each other (e.g., by being constrained within a delivery device), in order to reduce the delivery profile of the device. Referring now to FIG. 5C, during deployment of the arms inside the subject's ventricle, the support elements are separated from each other, e.g., by retracting a separation element 52 such that it is disposed between the support elements. Typically, while the above-described procedure is being performed, blood flow from the atrium to the ventricle continues via the separations between the support element, as indicated by blood flow arrow 42 in FIG. 5C.

The scope of the present application includes using chord-manipulation arms having any shape that would facilitate use of the chord-manipulation arms in the manner described herein. Typically, more than two arms (e.g., more than 4 arms) and/or fewer than 12 arms (e.g., fewer than 10 arms) are used. As described hereinabove, in accordance with respective applications, the arms are disposed at approximately 90 degrees (e.g. 90 degrees plus/minus 3 degrees, or exactly 90 degrees) with respect to the longitudinal axis of the distal-most portion of the delivery device, define an acute angle with respect to the longitudinal axis of the distal-most portion of the delivery device, or define an obtuse angle with respect to the longitudinal axis of the distal-most portion of the delivery device. For some applications, the arms are disposed at 45-135 degrees (e.g., 70-110 degrees, or 85-95 degrees) with respect to the longitudinal axis of the distal-most portion of the delivery device.

In accordance with the apparatus and techniques described hereinabove, chord-manipulation arms 26 may be used to perform any one of a number of functions. In accordance with some embodiments, such functions are performed in isolation from one another or in combination with one another. One such function is to use the arms to reduce the size of the atrioventricular valve annulus, by rotating the arms while the arms are deployed among chords. The rotation of the arms causes chords among which the arms are deployed to become deflected and, in turn, the deflection of the chords causes at least a portion of the atrioventricular valve (e.g., leaflets, and the annulus of the atrioventricular valve) to become twisted and pulled radially inwards toward the bases of the arms. A further function that the arms provide, in accordance with some applications of the present invention, is to provide a counterforce against which the annuloplasty ring is pushed. Yet another function that the arms, portions of the arms, and/or extensions of the arms provide, in accordance with some applications of the present invention, is to function as intraventricular anchoring portions, to which the annuloplasty ring becomes anchored, e.g., as described hereinabove with reference to FIGS. 1F-G.

As described hereinabove, in accordance with some applications of the present invention, an annuloplasty ring is implanted onto an atrioventricular valve annulus that is already reduced in size relative to its size prior to the initiation of the annuloplasty procedure. The scope of the present application includes, reducing the size of an atrioventricular valve annulus prior to implanting an annuloplasty ring (such that the annuloplasty ring is implanted onto an atrioventricular valve annulus that is already reduced in size), but using a different technique for reducing the size of the atrioventricular valve annulus to that described hereinabove.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for treating an atrioventricular valve of a heart of a mammalian subject, the atrioventricular valve including a valve annulus and valve leaflets between an atrium of a heart and a ventricle of the heart, chords, and papillary muscles, the apparatus comprising:
    an annuloplasty ring configured for implantation on the valve annulus in the atrium; and
    a plurality of chord-manipulation arms configured:
        for deployment, in the ventricle, among the chords of the atrioventricular valve;
        subsequently, to cause a size of the valve annulus to decrease, by rotating such as to twist the native atrioventricular valve and pull the native atrioventricular valve radially inwards, by deflecting the chords; and
        subsequently, to provide a counterforce, toward the atrium, against the annuloplasty ring during the implantation of the annuloplasty ring,
    wherein at least portions of the chord-manipulation arms are configured to remain under the atrioventricular valve leaflets and the annuloplasty ring is configured to become anchored to the portions of the chord-manipulation arms;
    wherein the portions are first portions, wherein the chord-manipulation arms further comprise second portions, and wherein the first portions of the chord-manipulation arms are configured to be detachable from the second portions of the chord-manipulation arms, and are configured to remain under the atrioventricular valve leaflets even after the second portions of the chord-manipulation arms are removed from the subject's ventricle.

2. The apparatus according to claim 1, wherein the chord-manipulation arms are configured, subsequently to the implantation, to untwist the native atrioventricular valve by rotating in an opposite direction to the direction of the rotation of the chord-manipulation arms that caused the native atrioventricular valve to become twisted.

3. The apparatus according to claim 1, wherein the atrioventricular valve includes a mitral valve, and the chord-manipulation arms are configured for deployment among chords of the mitral valve.

4. The apparatus according to claim 1, wherein the atrioventricular valve includes a tricuspid valve, and the chord-manipulation arms are configured for deployment among chords of the tricuspid valve.

5. The apparatus according to claim 1, wherein the chord-manipulation arms are sized such that, when disposed in radially-non-constrained configurations, the chord-manipulation arms span a diameter that is at least equal to an inner diameter of the annuloplasty ring, such that the chord-manipulation arms are configured to provide the counterforce during the implantation of the annuloplasty ring.

6. The apparatus according to claim 1, wherein the chord-manipulation arms are sized such that, when disposed in radially-non-constrained configurations, the chord-manipulation arms are configured to overlap radially with the annuloplasty ring, such that the chord-manipulation arms are configured to provide the counterforce during the implantation of the annuloplasty ring.

7. The apparatus according to claim 1, wherein at least a portion of an inner edge of each of the chord-manipulation arms is concavely curved in a given circumferential direction, and wherein the chord-manipulation arms are configured to pull the native atrioventricular valve radially inwards, by rotating in the given circumferential direction.

8. The apparatus according to claim 1, wherein the annuloplasty ring comprises a plurality of anchoring elements, and wherein at least some of the anchoring elements are configured to become embedded in the chord-manipulation arms.

9. The apparatus according to claim 1, further comprising a frame configured to extend from the ventricle into the atrium of the subject's heart, the frame defining holes which are sized such as to allow blood to flow from the atrium to the ventricle of the subject's heart via the frame, and wherein the chord-manipulation arms are coupled to a portion of the frame that is configured to be disposed within the ventricle.

10. The apparatus according to claim 1,
    further comprising a support rod and a hollow tube that define holes,
    wherein the chord-manipulation arms are coupled to the support rod and the support rod is configured to be disposed inside the hollow tube, and
    wherein the holes within the hollow tube are sized such as to allow blood to flow from the atrium of the subject's heart to the ventricle of the subject's heart via the hollow tube.

11. The apparatus according to claim 10, further comprising a unidirectional valve disposed within the hollow tube, and configured to allow blood flow from the atrium to the ventricle, but to block blood flow in the opposite direction.

12. The apparatus according to claim 1, further comprising a delivery device configured to deliver the chord-manipulation arms to the ventricle of the subject's heart, wherein the arms are disposed at an angle of between 45 degrees and 135 degrees with respect to a longitudinal axis of a distal-most portion of the delivery device.

13. The apparatus according to claim 1, further comprising a plurality of support elements, wherein each of the chord-manipulation arms is coupled to a respective one of the support elements, and wherein, during the deployment of the arms inside the ventricle, the support elements are configured to separate from each other.

14. A method for use with an annuloplasty ring, and an atrioventricular valve of a heart of a mammalian subject, the atrioventricular valve including a valve annulus and valve leaflets between an atrium of a heart and a ventricle of the heart, chords, and papillary muscles, the method comprising:
- deploying a plurality of chord-manipulation arms in the ventricle among the chords of the atrioventricular valve;
- subsequently rotating the arms, such that the arms cause a size of the valve annulus to decrease, by the arms twisting the native atrioventricular valve and pulling the native atrioventricular valve radially inwards, by deflecting the chords; and
- subsequently, implanting the annuloplasty ring on the valve annulus in the atrium, while using the arms (a) to maintain the size of the valve annulus at its decreased size, by maintaining the arms in their rotated state, and (b) to provide a counterforce, toward the atrium, against the annuloplasty ring, by pulling the arms from beneath the valve leaflets toward the annuloplasty ring.

15. The method according to claim 14, further comprising, subsequent to implanting the annuloplasty ring on the valve annulus, allowing the native atrioventricular valve to become untwisted by rotating the chord-manipulation arms in an opposite direction to the direction of the rotation of the chord-manipulation arms that caused the native atrioventricular valve to become twisted.

16. The method according to claim 14, wherein the atrioventricular valve includes a mitral valve, and deploying the plurality of chord-manipulation arms among the chords of the atrioventricular valve comprises deploying the plurality of chord-manipulation arms among chords of the mitral valve.

17. The method according to claim 14, wherein the atrioventricular valve includes a tricuspid valve, and deploying the plurality of chord-manipulation arms among the chords of the atrioventricular valve comprises deploying the plurality of chord-manipulation arms among chords of the tricuspid valve.

18. The method according to claim 14, wherein deploying the plurality of chord-manipulation arms among the chords of the atrioventricular valve comprises deploying the arms among the chords of the atrioventricular valve such that the arms span a diameter that is at least equal to an inner diameter of the annuloplasty ring, such that the arms are configured to provide a counterforce against which the annuloplasty ring is pushed, during implantation of the annuloplasty ring.

19. The method according to claim 14, wherein deploying the plurality of chord-manipulation arms among the chords of the atrioventricular valve comprises deploying the arms among the chords of the atrioventricular valve such that the arms overlap radially with the annuloplasty ring, such that the arms are configured to provide a counterforce against which the annuloplasty ring is pushed, during implantation of the annuloplasty ring.

* * * * *